Figure 1:
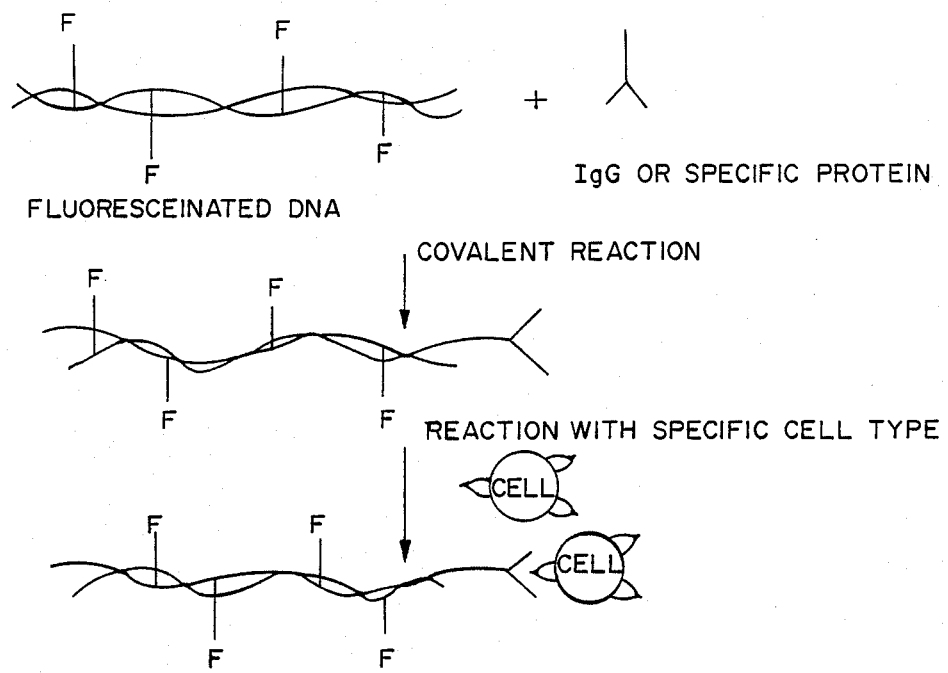

United States Patent [19]

Dattagupta et al.

[11] Patent Number: 4,824,775
[45] Date of Patent: Apr. 25, 1989

[54] CELLS LABELED WITH MULTIPLE FLUOROPHORES BOUND TO A NUCLEIC ACID CARRIER

[75] Inventors: Nanibhushan Dattagupta, New Haven; Michael E. Kamarck, Guilford, both of Conn.

[73] Assignee: Molecular Diagnostics, Inc., West Haven, Conn.

[21] Appl. No.: 688,493

[22] Filed: Jan. 3, 1985

[51] Int. Cl.[4] ............... C12Q 1/00; G01N 33/554
[52] U.S. Cl. .................................... 435/4; 435/6; 435/7; 435/29; 435/240.2; 435/243; 424/93; 514/2; 514/44; 436/519; 436/546
[58] Field of Search ........ 435/240, 241, 243, 253–258, 435/2, 4, 6–8, 29, 30, 172.3, 183, 188, 189, 948; 935/66, 70, 81; 424/85, 93, 94, 1.1; 436/518, 519, 528, 529, 543–548, 800, 804, 823, 828; 530/387–389, 402, 403, 405, 406; 536/27–29; 252/625, 645, 646, 301.16, 700

[56] References Cited

U.S. PATENT DOCUMENTS

| | | | |
|---|---|---|---|
| 4,469,796 | 9/1984 | Axen | 436/518 |
| 4,520,110 | 5/1985 | Stryer | 436/501 |
| 4,542,102 | 9/1985 | Dattagupta | 435/6 |
| 4,582,789 | 4/1986 | Sheldon, III | 435/6 |
| 4,587,044 | 5/1986 | Miller | 536/28 |
| 4,617,261 | 10/1986 | Sheldon, III | 435/6 |
| 4,626,501 | 12/1986 | Landes | 435/6 |
| 4,629,687 | 12/1986 | Schindler | 435/4 |

FOREIGN PATENT DOCUMENTS 0063879 11/1982 European Pat. Off. .
0128332 12/1984 European Pat. Off. .

OTHER PUBLICATIONS

Loken et al., Ann. N.Y. Acad. of Sci., 254, 163–171 (1975).
Aguet, M., Nature 284, 459–461 (1980).
Reinherz, E. L. and Schlossman, S. F., Immunol. Today 2, 69–75 (1981).
Oi et al., J. Cell. Biol. 93, 981–6 (1982).
J. W. Goding: Use of Staphyloccocal Protein A as an Immunological Reagent, J. Imm. Methods 20, 241–253 (1978).

*Primary Examiner*—Margaret Moskowitz
*Attorney, Agent, or Firm*—Sprung, Horn, Kramer & Woods

[57] ABSTRACT

In passing labeled cells through a cell sorter, the improvement which comprises employing a labeled cell comprising a cell, an antibody specific to and bound to such cell, a nucleic acid fragment joined to said antibody, and a plurality of labels on said nucleic acid fragment. Because of the presence of multiple labels, the sensitivity of the separation of labeled cells is increased.

5 Claims, 1 Drawing Sheet

CELLS LABELED WITH MULTIPLE FLUOROPHORES BOUND TO A NUCLEIC ACID CARRIER

The present invention relates to the labeling of cells so they can be assayed by a cell sorter.

In cell-biological investigations, identification of different kinds of cells is usually carried out by labeling the cells with specific reagents When coupled with other technologies, specific staining methods can also be used for separation and identification of different cells in a mixture of cells. These methods are entirely dependent on the specific recognition of the stain by the cell type. The most specific of these reagents is an antibody which is specific for a surface component of the cell to be detected or separated. Specific antibodies to cell surface molecules have been particularly useful in subsetting circulating leukocytes of human and mouse. Specific monoclonal antibodies which identify subpopulations of T-lymphocytes, B-lymphocytes and macrophages have been widely used in conjunction with flow cytometric methods to accurately quantitate circulating lymphoid populations. In somatic cell genetics, where transfer of a specific DNA fragment to a cell is essential for cloning and/or expression of the gene, separation of cells containing the introduced gene from the rest of the cells is desirable. Although the detection of the expressed gene can be carried out by monitoring the activity of the new protein made by the cells, separation cannot be done without the use of specific and sensitive reagents. The reagents which are used at present include fluorescently labeled antibodies.

The specificity of antibodies is essentially unlimited, but approximately 5000 fluorophores have to be bound to each cell for detection by sensitive fluorimeters such as the fluorescence-activated cell sorter. (Loken et al, Ann. N.Y. Acad. of Sci., 254, 163 (1975)). Many important cell surface molecules, such as growth receptors critical in cell division control, however, may be present in numbers lower than 5000/cell. For example, the interferon receptor is probably expressed at 2000 molecules/cell or less (Agnet, Nature 284, 459 (1980) and therefore cannot presently be detected by antibody based methods.

In addition, lymphoid subpopulation analysis has revealed that both quantitative differences in cell surface antigen expression and the simultaneous expression of other antigens on the same cell are biologically significant. Two, three and even four immunofluorescence measurements, each defining a specific antigen, may be necessary to identify the function of a cell.

Detection of multiple determinants on a single cell is increasingly important to medical applications as has been described for the analysis of human lymphocyte subpopulations. (Reinherz, E. L. and Schlossman, S. F. Immunol. Today 2, 69 (1981). To detect two or three determinants simultaneously, one must either divide up the emission signal, losing sensitivity or excite fluorochrome at suboptional spectral lines, losing sensitivity. An alternative to dividing up the emission signal is the use of a second laser and addition of electronics equipment which is extremely costly.

The fluorophores most commonly used for antibody derivatization are fluorescein, rhodamine, and the phycobiliproteins, (see Oi et al., J. cell., biol. 93, 981 (1982) and references therein). Among the fluorophores, phycobiliproteins are the most sensitive probes, as multiple fluorophores are present per molecule. Furthermore, a number of different excitation/emission fluorochromes are available, facilitating detection of two and three fluorescence emissions simultaneously. The apparent disadvantage of phycobiliproteins is the high molecular weight of these proteins and their solubility which may interfere with the antigen-antibody reaction. The maximum number of fluorophores available per molecule is also fixed. Because of their size and solubility properties, it is difficult to derivatize the phycobiliproteins efficiently to antibodies without affecting the property of the latter. Furthermore, although phycobiliproteins are currently the most sensitive probes, they may still be insufficiently sensitive. In addition, there are only a few types of fluorophores available in the phycobiliproteins. Therefore, there is a limitation of the excitation/emission wavelengths which can be utilized.

Application Ser. No. 513,932, filed July 14, 1983, now abandoned, discloses a photochemical method of labeling nucleic acids. The invention, preferably employed for detection purposes in hybridization assays, can be used in immunological assays. The labeling employs a photoreactive furocoumarin or phenanthridium compound to link the nucleic acid to a label which can be assayed in a conventional manner. The end product is thus a labeled nucleic acid probe comprising (a) a nucleic acid component, (b) a furocoumarin or phenanthridium compound photochemically linked to the nucleic acid component, and (c) a label chemically linked to (b). For coupling to DNA, aminomethyl trioxsalen, aminomethyl angelicin and amino alkyl ethidium or methidium azides are the preferred compounds. The nucleic acid component can be single or double stranded DNA or RNA or fragments thereof. The label can be anything which can be asayed in a known manner.

U.S. Pat. No. 4,670,380 discloses a detection probe comprising a particular oligo or polynucleotide sequence, enzymatically coupled at one end to a nucleotide which contains a readable label. The coupled nucleotide can be a polyribonucleotide coupled to the 5' end of the oligo or polynucleotide probe by an enzyme such as T4 RNA ligase and can be directly readable. Alternatively, the nucleotide can be coupled to the 3' end by a terminal deoxynucleotidyl transferase. If the nucleotide is a triphosphate such as etheno ATP or CTP, the nucleotide triphosphate will be fluorescent and therefore, directly readable. The nucleotide triphosphate can contain a Hg or SH radical on the purine or pyrimidine ring, which can be read chemically or preferably could be further labeled, for example, with a hapten, fluorophore or enzyme. Although the invention is preferably employed for detection probes in hybridization assays, it can also be employed in immunological assays.

Application Ser. No. 582,503, filed Feb. 22, 1984, now pending, discloses a nucleic acid probe coupled to a solid support via a single chemical covalent linkage. A specific embodiment of the invention entails the conjugation of a solid support containing a reactive NH$_2$ group to the nucleic acid, to yield a nucleic acid joined to a solid support via an amine linkage.

It is an object of the invention to provide a means of labeling immunological reagents with multiple labels, i.e., 20 or more labels per protein molecule, resulting in a reagent which is highly sensitive for cell sorting purposes and free of the disadvantages noted hereinabove.

It is another object of the invention to label an immunological reagent in such way that there is no interference with immunological reaction.

These and other objects and advantages are realized in accordance with the present invention pursuant to which there is provided a labeled cell comprising a cell, an antibody specific to and bound to such cell, a nucleic acid fragment joined to the antibody, and a plurality of labels on the nucleic acid fragment.

The nucleic acid is the label carrier. Since polynucleotides can be covalently modified to carry large numbers of fluorescent molecules, they serve as a matrix for multiple labeling. A nucleic acid molecule is heavily labeled with a fluorescnt molecule. Then the labeled nucleic acid is covalently linked to a protein, for example, protein A.

The covalently coupled protein-nucleic acid can carry a large number of labels, on the nucleic acid, advantageously applied before the covalent coupling and before use of the coupled material in a cell sorter.

The labels may be of any known types of fluorophores.

In use, the protein moiety of the coupled material is specific for some other reagent such as another protein, a specific nucleotide sequence of a nucleic acid or a hapten. Through this specificity, in effect, the labels become "attached" to the site to which the protein specifically binds.

The invention also extends to the process of conducting an assay for a specific cell type, as determined by the presence of a label.

Describing the invention in greater detail, the protein component can be of many diverse kinds, provided it is site specific. Particularly suitable materials include immunoglobulins, protein A, and the like. Protein A is a 40,000 Dalton single chain polypeptide isolated from *Staphylococcus aureus.* In some strains of *S. aureus,* it is covalently linked to the peptidoglycan part of the cell wall. Protein A binds to several IgG classes of antibodies through Fc-binding regions. In this case, the antibodies are specific for the antigen to be detected in the test sample. Protein A is very stable to heat and denaturing agents and can be renatured following denaturing conditions. [Review: J. W. Goding: Use of Staphylococcal Protein A as an Immunological Reagent, J. Imm. Methods 20, 241–253 (1978).]The binding of protein A to IgG does not affect the antigen binding site of the IgG molecule.

Alternatively, the protein moiety can be an antibody such as IgG and will thus be specific for some antigen on the cell surface.

The antibody has the specificity for a particular antigen. The antibody can be either a monoclonal or polyclonal. The antibody can be produced in vivo by a number of species or in vitro by cell culture or recombinant DNA technology.

The nucleic acid can be singly or double stranded DNA, RNA, DNA-RNA hybrid, oligoribonucleotide or oligodeoxyribonucleotide.

The protein can be covalently coupled to the nucleic acid in various ways. In one procedure, one end of the nucleic acid is modified as with a terminal transferase so as to establish a ribonucleotide end, if not already present. The ribonucleotide end can be oxidized with periodate to form terminal aldehyde groups which can undergo a Schiff's base reaction with an amino-group of the protein, followed by hydrogenation to form a stable aminomethyl linkage between the protein and nucleic acid.

The label can be applied to the nucleic acid moiety before or after coupling to the protein and even at a much later stage in the assay. Because of its presence on the nucleic acid, the label will not interfere with the reactions of the protein moiety even though many labels may be present per protein moiety, e.g., 20, 100 or even more. It has been previously shown that if certain proteins are directly labeled, as few as 6 labels are enough to interfere with the reaction.

The label can be attached to the nucleic acid as described in detail in application Ser. No. 513,932. abandoned and U.S. Pat. No. 4,670,380 supra. Representative labels include fluorophores, for example, fluorescein, texas red, rhodamine or phycoerythrine, and hapten such as biotin.

As noted, the protein moiety should be site specific, as for example, to the Fc portion of an antibody such as IgG.

More specifically, the invention can be illustratively described as follows: A well defined linear double stranded DNA fragment is attached to a specific protein, e.g., protein A, or a specific antibody which recognizes a cell surface molecule The DNA with the attached protein is then labeled with a fluorophore via a specific reaction which modifies only the DNA so that multiple copies of the label will be on the DNA. The reaction is chosen in such a fashion that only a few copies of the label can be attached to the protein. Then this DNA-protein reagent which is labeled with multiple copies of the fluorophore is reacted with the cell and the bound cells are separated from the unbound cells on a cell sorter. The coupling reaction between the protein and DNA can be specific at the 3' or 5' end of the DNA or can be nonspecific, such as the reaction mediated by glutaraldehyde. The specific reaction is carried out by derivatizing DNA with a proper enzyme to introduce a specific nucleotide residue at one end. For example, by using terminal deoxynucleotidyl transferase, a ribonucleotide residue can be coupled to the 3' end of a DNA fragment. Then this can be oxidized with periodate to produce a dialdehyde. The resulting dialdehyde will efficiently react with a protein and, after borohydride reduction, a stable DNA-protein linkage can be generated. This and other procedures have been described in detail in Applications Serial Nos. 582,503 and 588,858, now pending. After the protein DNA conjugate is formed, the DNA region is reacted with a DNA specific intercalator carrying a primary amine residue. The intercalators are then covalently linked to DNA bases by irradiation. The (DNA-intercalator-protein) adduct is then reacted with an activated fluorescent compound, e.g., fluorescein isothiocyanate. Although some of the labels will react with proteins, many of the will react with the primary amine available on DNA. The order of the coupling process can be altered to avoid any reaction of the fluorophoes with protein. By this method, the number of fluorophore and the type of fluorophore can be altered in many different ways. By adjusting the length of the DNA molecule, it is believed possible to couple up to several hundred fluorescent moieties per protein. The nucleic acids can be linear, circular, ribo-, deoxy ribo- hybrid polymer, double stranded polyribonucleic acid or deoxyribonucleic acids. The intercalator can be any molecule which can be inserted specifically into DNA.

A preferred process of preparing the labeled cells is diagrammatically illustrated in FIG. 1:

The advantages of the present invention are as follows:

(1) The number of fluorophores is not limited; multiple copies of phycobiliproteins can also be coupled.
(2) The nucleic acids being anionic, polyelectrolyte solubility is high.
(3) Double stranded nucleic acids are not globular and hence interference with antigen-antibody reaction will be minimum.
(4) Negative charge of the nucleic acids can be used directly for separation.
(5) The method can be used to localize a specific DNA fragment on the cell surface. The specific localization may eventually be useful for gene transfer processes.

The invention will be further described in the following illustrative examples wherein all parts are by weight unless otherwise expressed.

EXAMPLE 1

Terminal transferase reaction to couple ribose residue at the end of DNA.

Hae III digest of QX 174 RF is dialyzed against potassium cacodylate buffer (pH 7.2; 200 mM) and the concentration is adjusted to $10^{-4}$ M in base pairs. To the DNA solution (100 μl), 5 μl 2 mM dithiothreitol 1 μl 10 mM ATP mixed with $^{14}$C labeled ATP and 10 μl mM cobalt chloride are added. The mixture is incubated at 37° C. for 5 minutes and then chilled in ice for 10 minutes. 15 units of terminal deoxynucleotidyl transferase is added and the mixture incubated at 15° C. for 60 minutes. After the reaction, the enzyme is removed by phenol extraction and the unreacted nucleotides are removed by dialysis or passage through a Sephadex G-50 column. The yield is calculated from the absorbance to CPM ratio. Assuming uniform reaction, the yield is about 10-20 ATP residues per 3' end of the DNA. (For RNA-DNA hybrid or double stranded RNA, this step of TdT reaction is not required for further reaction.)

EXAMPLE 2

Oxidation and coupling of proteins

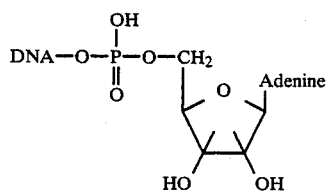

0.1 M sodium acetate pH 5; 0.1 volume 1 M sodium periodate

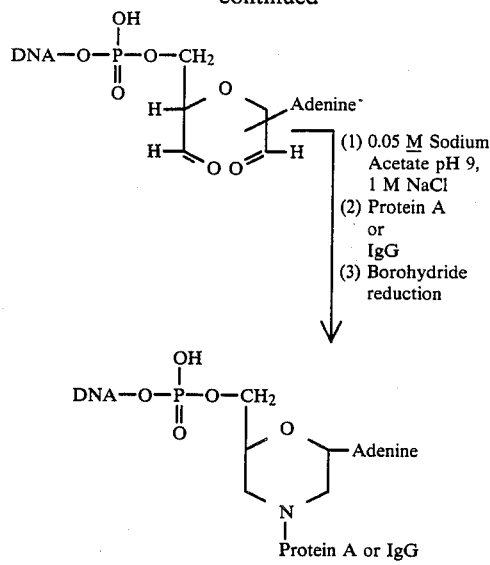

(1) 0.05 M Sodium Acetate pH 9, 1 M NaCl
(2) Protein A or IgG
(3) Borohydride reduction The oxidation of the ribose end of the product of Example 1 is effected with sodium periodate at room temperature using 0.1 M sodium acetate buffer pH 5 and 0.1 volume 1 M sodium periodate. The resulting solution is dialyzed to remove excess periodate against 1 M NaCl, 0.05 M sodium acetette pH 9. Then protein A or IgG is added and the solution is reduced by adding Na-borohydride.

The reaction can be carried out between 0.50° C. and in ionic strength up to 1 M NaCl.

EXAMPLE 3

Covalent reaction between double stranded nucleic acids and aminomethyl trioxsalen Hae III restriction enzyme di.=st of QX174 RF double stranded DNA or the product of Example 1 is dissolved in or dialyzed against Tris-EDTA buffer (TE) (10 mM trishydroxymethyl aminomethane, 1 mM EDTA; pH 7.1 adjusted with HCl). The concentration is adjusted to $1.5 \times 10^{-4}$ M/1 in base pairs. 4'-aminomethyl trioxsalen dissolved in TE is added so that the ratio of the ligand to base pairs is 0.1. The mixture is flushed with nitrogen gas for 15 seconds and irradiated at 360 nm radiation for 60 minutes. This causes the trioxsalen residues to bind the DNA covalently. After the reaction, the mixture is precipitated with ethanol after adding sodium acetate to raise the ionic strength. The precipitation also leaves any unreacted trioxsalen in the supernatant. By using tritiated trioxsalens, the relative amount of coupling can be estimated. (Exactly dentical conditions can be employed for double stranded RNA and RNA-DNA hybrids).

EXAMPLE 4

Labeling of products of Example 2 and 3

The products of Examples 2 and 3 have free primary NH$_2$ residues from AMT and/or protein. They are reacted with biotin and/or fluorescein or rhodamine. An example is provided with fluorescein. A fluorescein isothiocyante (FITC) solution is prepared by dissolving 5 mg of the solid in 2 ml ethanol. Products of Examples 2 and 3 are dialyzed again or dissolved in 0.1 M sodium bicarbonate buffer (pH 8-9). Then they are mixed with the ethanolic solution of FITC in 15:1 volume ratio with equal weight concentration. The reaction is allowed to proceed for one hour. The product is purified on Sephadex G50 column. The excluded volume fractions contain the product.

Alternative labeling with biotin is done by using N-hydroxysuccinimido biotin as described in application Ser. No. 513,932, filed July 14, 1983, now pending.

EXAMPLE 5

Use of protein A-fluoresceinated DNA for cell sorter separation of mouse α cells expressing human 4F2 antigens following transfection with human genomic DNA The first step on surface antigen cloning Human genomic DNA and Herpes simplex virus thymidine kinase genes are cotransfected into mouse αtk cells as has been described (Kuhn et al. Mol. Biol. Med. 1, 335 (1983)) and Hypoxanthine-Aminopterin-thymidine (HAT) resistant clones are selected. Transformants are then stained by indirect immunofluorescence (Kamarck et al., Somatic Cell Genetics 8, 385 (1982)).

Tissue culture cells are detached from flasks using phosphate buffered saline with 0.03% EDTA and washed three times with alpha-MEM with 2% heat inactivated fetal calf serum (FCS). Test cells ($2 \times 10^6$) are incubated at 4° C. for 45 minutes with excess antiserum against the 4F2 antigen in a volume of 50 μl. Cells are washed three times with phosphate buffered saline and incubated at 4° C. for 45 minutes with 2 μl of the protein A-fluoresceinated DNA conjugates (~1 mg protein A/ml) of Example 4 or 2 μl of protein A labeled directly with FITC for comparison. Cells were finally washed by centrifugation through 4 ml of heat inactivated fetal calf serum. Normal serum controls were used in parallel to evaluate the level of autofluorescence and nonspecific staining.

Quantitative evaluation of immunofluorescence was performed in a fluorescence activated cell sorter (FACS IV, Becton Dickinson Electronics LAB, Mountain View, Calif.). Efficient transmittance of fluorescent light was achieved with a 530/30 band pass filter. Data were collected using a logarithmic amplifier and evaluated using the consort 40 FACS computer. The histograms displayed present increasing fluorescence on the x-axis and cell number on the y axis. The results indicate that the reagent described in the invention is useful for cell sorting purposes as determined both by the level of fluorescence achieved and in the case of discriminating low frequency antigen positive cells.

It will be understood that the specification and examples are illustrative but not limitative of the present invention and that other embodiments within the spirit and scope of the invention will suggest themselves to those skilled in the art.

We claim:

1. A labeled cell consisting essentially of a cell, an antibody specific to and bound to such cell, a nucleic acid fragment covalently coupled to said antibody, and a plurality of fluorophores on said nucleic acid fragment, wherein said fluorophores are coupled to said nucleic acid fragment via a nucleic acid specific intercalator carrying a primary amine residue.

2. A labeled cell according to claim 1, wherein said fragment is specifically bound to said antibody.

3. A labeled cell according to claim 2, wherein said fragment is covalently coupled to a protein which protein is specifically bound to the antibody.

4. A process for producing a labeled cell according to claim 1 consisting essentially of coupling multiple fluorophore labels to a nucleic acid fragment via a nucleic acid specific intercalator carrying a primary amine residue, covalently coupling said labeled fragment to an antibody specific to a particular cell, and binding said antibody to said cell.

5. In a method of passing labeled cells through a cell sorter, detecting the labeled cells and sorting out the cells on the basis of their labels, the improvement which comprises employed labeled cells according to claim 1.

* * * * *

UNITED STATES PATENT AND TRADEMARK OFFICE
CERTIFICATE OF CORRECTION

PATENT NO. : 4,824,775
DATED : April 25, 1989
INVENTOR(S) : Nanibhushan Dattagupta, et al It is certified that error appears in the above-identified patent and that said Letters Patent is hereby corrected as shown below:

| | |
|---|---|
| Col. 1, line 43 | Delete "Agnet" and substitute --Aguet-- |
| Col. 3, line 14 | Correct spelling of --fluorescent-- |
| Col. 4, line 26 | Insert --.-- after "molecule" |
| Col. 4, line 56 | Delete "the" and substitute --them-- |
| Col. 6, line 6 | In formula insert --H-- before -- /Adenine-- |
| Col. 6, line 39 | Delete "di.=st" and substitute --digest-- |
| Col. 8, line 41 | Delete "employed" and substitute --employing-- |

Signed and Sealed this

Twenty-eighth Day of August, 1990

Attest:

HARRY F. MANBECK, JR.

*Attesting Officer*     *Commissioner of Patents and Trademarks*